United States Patent [19]

Knoll et al.

[11] Patent Number: 5,220,068
[45] Date of Patent: Jun. 15, 1993

[54] PSYCHOSTIMULANT AGENT

[75] Inventors: József Knoll; Antal Simay; Éva Szinnyei; Éva Somfai; Zoltán Török, all of Budapest; Károly Mozsolits, Sopron; János Bergmann, Visergád, all of Hungary

[73] Assignee: Chinoin Gyogyszer - es Vegyeszeti Termekek Gyara Rt., Buadpest, Hungary

[21] Appl. No.: 649,239

[22] Filed: Jan. 29, 1991

Related U.S. Application Data

[63] Continuation of Ser. No. 269,665, Jul. 15, 1988, abandoned.

[30] Foreign Application Priority Data

Sep. 25, 1986 [HU] Hungary .............................. 4101/86

[51] Int. Cl.[5] .................. C07C 211/27; A61K 31/135
[52] U.S. Cl. ................................... 564/381; 564/375; 564/376; 564/382
[58] Field of Search ...................... 564/381, 382, 374; 514/654

[56] References Cited

U.S. PATENT DOCUMENTS 2,597,247  5/1952  Kerwin et al. .................. 260/570.8

(List continued on next page.)

FOREIGN PATENT DOCUMENTS 318558 10/1974 Austria .

(List continued on next page.)

OTHER PUBLICATIONS

E. Binder et al "Austria-Codex Fachinformation 1986/87" pub. 1986, Osterreichischer Apotheker-Verlag (Wien), see pp. 1010–101 Segontin-Dragees 60 mg. The text is same as Austria-Codex 1984/85.

(List continued on next page.)

Primary Examiner—Richard L. Raymond
Assistant Examiner—P. O'Sullivan
Attorney, Agent, or Firm—Herbert Dubno; Jonathan Myers

[57] ABSTRACT

The present invention relates to a pharmaceutical composition comprising as active ingredient a compound of the Formula I

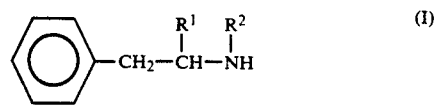

wherein
$R^1$ stands for straight or branched chain alkyl comprising 1 to 8 carbon atoms; phenyl alkyl having 7 to 10 carbon atoms; phenyl; or cycloalkyl comprising 3 to 8 carbon atoms;
$R^2$ stands for straight or branched chain alkyl comprising 1 to 8 carbon atoms; alkyl comprising 1 to 8 carbon atoms substituted by halogen, hydroxy, alkoxy having 1 to 4 carbon atoms or by one or two phenyl groups; phenyl; or cycloalkyl having 3 to 8 carbon atoms, with the proviso that groups $R^1$ and $R^2$ together contain at least three carbon atoms. The invention also relates to a process for the preparation of compounds of the Formula I by methods known per se. The compounds of the Formula I are phychostimulants having a new spectrum of effect which can be used in therapy for increasing psychical activity (learning and retention) and for treating clinical patterns of depression and deficiencies of learning and retention like in Alzheimer's disease, and are void of side effects (e.g. due to catecholamine release) of known stimulants.

4 Claims, No Drawings

U.S. PATENT DOCUMENTS

| | | |
|---|---|---|
| 2,797,242 | 6/1957 | Edgerton et al. ............... 260/570.8 |
| 3,014,966 | 12/1961 | Freifelder et al. ................ 260/563 |
| 3,445,518 | 5/1964 | Shavel, Jr. et al. ............. 260/570.8 |
| 3,485,926 | 12/1969 | Schuler et al. ...................... 424/330 |
| 3,911,016 | 10/1975 | Klingler et al. ................. 260/570.8 |
| 4,025,624 | 5/1977 | Alphin et al. ....................... 424/233 |
| 4,404,222 | 12/1980 | Baker et al. ......................... 424/304 |

FOREIGN PATENT DOCUMENTS

| | | |
|---|---|---|
| 767263 | 4/1941 | Fed. Rep. of Germany . |
| 893341 | 10/1953 | Fed. Rep. of Germany . |
| 1133395 | 1/1963 | Fed. Rep. of Germany . |
| 1227447 | 5/1967 | Fed. Rep. of Germany . |
| 145599 | 12/1980 | Fed. Rep. of Germany . |
| 1478311 | 4/1967 | France . |
| 0814339 | 6/1959 | United Kingdom . |
| 1142981 | 2/1969 | United Kingdom . |
| 967871 | 8/1969 | United Kingdom . |
| 1218135 | 1/1971 | United Kingdom . |

OTHER PUBLICATIONS

Hans G. Boit, "*Beilsteins Handbook der Organischen Chemic*" 4th ed., vol. 12, suppl. vol. 3, (1973) Sprie,er--Verlag, pp. 2668–2671, 2717, 2748, 2760, 2761.

Chem. Abstracts, vol. 98, No. 15, 119164 (1983).

R. Luckenbach, "Beilsteins Handbook der Organischen Chemic", 4th edition, vol. 12, Supplement vol. 4, published 1984, Sprie,er-Verlag, pp. 2591, 2592, 2594, 2596, 2811.

D. Seebach et al, "Lithierungund Elektrophile Substitution an alpha-Methylene-gruppen von Nitrosaminen" Chemische Berichte, vol. 110, 1977, Verlag Chemic GmbH, pp. 1852–1865.

PSYCHOSTIMULANT AGENT

This is a continuation of co-pending application Ser. No. 07/269,665 filed on 15 Jul. 1988, now abandoned.

CROSS REFERENCE TO RELATED APPLICATION

This application is a National Phase Application of PCT HU 87/00040, filed 25 Sep. 1987 and based upon Hungarian National Application 4101/86 of 25 Sep. 1986 under the International Convention.

FIELD OF THE INVENTION

This invention relates to pharmaceutical compositions stimulating the central nervous system and having a new spectrum of activity, new phenylakylamine derivatives which can be used as active ingredient in such pharmaceutical compositions, a process for the preparation of the such active ingredients and pharmaceutical compositions and the use of the new phenylalkylamine derivatives and pharmaceutical compositions comprising the same for stimulating the central nervous system.

The pharmaceutical compositions of the present invention exhibit their activity in the organism mainly by inhibiting the neuronal uptake of biogenic amines.

BACKGROUND OF THE INVENTION

It is known that the most important dose-dependent effect of the so-called indirectly acting sympathomimetic amines belonging chemically to the class of phenylakylamines (e.g. the endogenous phenyl ethylamine (PEA) and tyramine) resides in the release of catecholamines—especially noradrenaline from the plasma stores of the neurons. Other non-endogenous phenylakylamines (e.g. amphetamine and metamphetamine) possess similar properties. Moreover, the noradrenaline releasing effect and depending on the dose the effects of other transmitter amines (e.g. serotonin) is strong and long lasting for metabolic reasons. Metamphetamine, also inhibits the neuronal uptake of indirectly acting endogenous sympathomimetic amines to a significant extent, but this effect is completely suppressed by noradrenaline release under in vivo conditions.

DESCRIPTION OF THE INVENTION

The present invention is based on the discovery that in the class of phenyl alkylamines a suitable modification of the chemical structure can completely eliminate the known characteristic and dominant effect of this compound group namely the effect of inducing the outflow of transmitter amines and can strengthen a hitherto subordinated effect of this compound group namely the inhibition of neuronal uptake of sympathomimetic amines, in a selective manner. Thus stimulants having a new spectrum of activity can be obtained.

According to the present invention there are provided biologically active phenyl alkylamines of the Formula I, salts thereof, processes for the preparation of the compounds, pharmaceutical compositions comprising as active ingredient the said compounds or salts thereof and the use of the compounds or pharmaceutical compositions comprising the same.

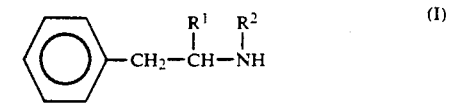

In the present specification the substituent definitions of the Formulae is as follows:

$R^1$ stands for straight or branched chain alkyl comprising 1 to 8 carbon atoms; phenylakyl having 7 to 10 carbon atoms; phenyl; or cycloalkyl comprising 3 to 8 carbon atoms;

$R^2$ stands for straight or branched chain alkyl comprising 1 to 8 carbon atoms; alkyl comprising 1 to 8 carbon atoms substituted by halogen, hydroxy, alkoxy having 1 to 4 carbon atoms or by one or two phenyl groups; phenyl; or cycloalkyl having 3 to 8 carbon atoms, so that groups $R^1$ and $R^2$ together contain at least three carbon atoms;

$R^3$ stands for straight or branched chain alkyl comprising 2 to 8 carbon atoms; phenyl alkyl having 7 to 10 carbon atoms; phenyl; or cycloalkyl comprising 3 to 8 carbon atoms; and $R^4$ stands for straight or branched chain alkyl comprising 1 to 8 carbon atoms; alkyl having 1 to 8 carbon atoms substituted by halogen, hydroxy, alkoxy having 1 to 4 carbon atoms or by one or two phenyl groups; phenyl; or cycloalkyl having 3 to 8 carbon atoms;

so that $R^3$ and $R^4$ together contain at least 5 carbon atoms; but when $R^3$ stands for methyl, $R^4$ is other than benzyl; and further so that if $R^3$ stands for ethyl, $R^4$ is other than isobutyl.

A and B stand for groups which are capable of forming a $-NH-R^2$ group when reacting with each other or comprise this latter group and;

X stands for halogen or a sulfonic acid ester group.

The present invention comprises a process for the preparation of compounds of the Formula I and salts thereof which comprises reacting a compound of the Formula II

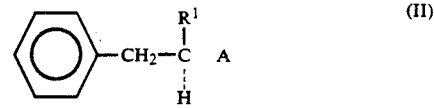

with a compound of the Formula III B—$R^2$ (in which Formulae $R^1$ and $R^2$ are as stated above and A and B stand for groups which are either capable of forming a $-NH-R^2$ group when reacting with each other or comprise the said group) and thereafter if desired converting the compound of the Formula I into a salt formed with an organic or inorganic acid and/or liberating a compound of the Formula I from a salt and if desired finishing a compound of the Formula I or a salt thereof in the form of a pharmaceutical composition by methods known per se.

Thus the compounds of the Formula I can be prepared by reacting a ketone of the Formula IV

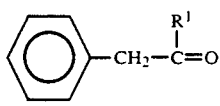 (IV)

with an amine of the Formula V H$_2$N—R$^2$ and reducing the ketimine intermediate formed without or after isolation. The reduction can be carried out by methods known per se, e.g. by catalytic hydrogenation (preferably in the presence of a palladium or Raney-nickel catalyst) or by using a complex metal hydride (e.g. sodium borohydride) or with the aid of a conventional chemical reducing agent (e.g. sodium dithionite or amalgamated aluminum).

According to a further realization of the process of the present invention a compound of the Formula VII

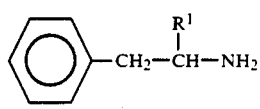 (VII)

is reacted with an alkylating agent of the Formula VI,

X—R$^2$ (VI)

or an amine of the Formula V is alkylated with a compound of the Formula VIII.

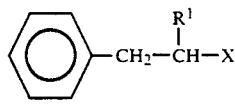 (VIII)

The said reactions can preferably be carried out in the presence of an acid binding agent. For this purpose an excess of the amine starting material may serve or an organic or inorganic base (e.g. triethylamine or potassium carbonate) or a basic ion-exchanging resin can be used.

The compounds of Formula XI

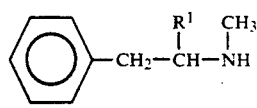 (XI)

can be prepared by methylating a compound of the Formula VII by reacting the same with formaldehyde and formic acid.

Th compounds of the Formula I prepared by the process of the present invention are in the free base form lipoid-soluble oily substances which can be—if desired—converted into crystalline water-soluble salts. Salt formation can be carried out by using pharmaceutically acceptable inorganic or organic acids (e.g. hydrochloric acid, hydrobromic acid, sulfuric acid, phosphoric acid, formic acid, acetic acid, oxalic acid, maleic acid etc). The compounds of the Formula I can be liberated from the acid addition salts by conventional methods. The compounds of the Formula I and biologically acceptable acid addition salts thereof can be used as active ingredients in the preparation of human pharmaceutical composition.

According to a further aspect of the present invention there are provided pharmaceutical compositions comprising as active ingredient at least one compound of the Formula I or a pharmaceutically acceptable acid addition salt thereof.

A particularly desirable compound is the compound of Formula XII

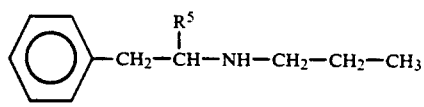 (XII)

where R$^5$ is alkyl having 2–4 carbon atoms.

According to a still further aspect of the present invention there is provided a process for the preparation of pharmaceutical compositions which comprises admixing a compound of the Formula I or a pharmaceutically acceptable acid addition salt thereof with suitable inert pharmaceutical carriers.

The pharmaceutical compositions can be prepared by known methods of the pharmaceutical industry. The active ingredient can be finished in the conventional dosage forms (e.g. tablets, pills, coated pills, dragées, capsules, injections etc). The pharmaceutical compositions can comprise the usual carriers, additives, sliding agents, fillers, auxiliary agents etc.

The compounds of the Formula I significantly inhibit the tyramine-induced noradrenaline release from the plasma pores of neurons by inhibiting the tyramine uptake. As opposed to known phenyl alkylamines the compounds of the Formula I do not exhibit a noradrenaline releasing effect. At the same time the compounds of the Formula I strongly inhibit the neuronal uptake of noradrenaline and copamine, considerably increase the catecholaminergic activity, but—contrary to amphetamine and methamphetamine—do not influence serotonergic activity even if administered at high doses.

The compounds of the Formula I are stimulants of the central nervous system which show a stimulating effect in learning and antidepressive pharmacological tests, increase motility and metabolism only to a moderate extent, exert no considerable anorectic effect and are but slightly toxic.

Contrary to a main group of known psychoenergetic agents, the compounds of the Formula I are devoid of MAO inhibiting activity and are—concerning their mechanism of activity and chemical structure—considerably different from known tricyclic antidepressants too.

It can be declared on the basis of the aforesaid that the phenyl alkylamines of the Formula I constitute a psychopharmacone group of a new mechanism of effect, being suitable for increasing physical activity (learning, memory storing) and for the medical treatment of clinical patterns of depression as well as diseases with significant learning and memory deficits likes Alzheimer's disease, presumably without exhibiting the side-effects of known stimulants which cause catecholamine release.

According to a still further aspect of the present invention there is provided a method of treatment which comprises treating healthy or ill humans with a pharmaceutical composition containing an effective amount of a compound of the Formula I or a pharmaceutically acceptable acid addition salt thereof.

The preferred daily dose amounts of from about 10 mg to about 150 mg, particularly to about 30 mg. The pharmaceutical compositions may be administered preferably orally, parenterally or by the sublingual route.

Due to their low toxicity the compounds of the Formula I can also be used in pediatrics, in a suitable trans-calculated dose.

The suitable veterinary dose amounts to 2-8 mg/kg.

The compounds of the Formula IX form a sub-group of the compounds of the Formula I being new and never disclosed in the prior art.

SPECIFIC EXAMPLES

Examples without limiting the scope of protection to the Examples.

Chemical examples

EXAMPLE 1

To a solution of 16.2 g (0.1 mole) of benzyl-propyl-ketone in 200 ml of methanol 23.6 g (0.4 mole) of isopropyl amine and 6 g of a 5% palladium/charcoal catalyst are added and the reaction mixture is hydrogenated under a pressure of 7-10 atm. under shaking. After the uptake of the calculated amount of hydrogen the reaction mixture is filtered, the filtrate is evaporated and the residue dissolved in ethanol comprising hydrochloric acid. The mixture is evaporated. The residual N-isopropyl-1-phenyl-2-pentylamine-hydrochloride can be purified by recrystallization. Mp.: 136°-139° C.

EXAMPLE 2

To a solution of 16.2 g (0.1 mole) of benzyl-propyl-ketone in 30 ml of methanol a solution of 7.5 g (0.1 mole) of 3-propanol-amine and 20 ml of methanol is added. The mixture is allowed to stand, whereupon 1.9 g of sodium borohydride are added, the reaction mixture is allowed again to stand and then evaporated. The residue is taken up in water, extracted with benzene, the benzene solution is dried and evaporated. The residual cruse N-(3-hydroxypropyl)-1-phenyl-2-pentylamine is purified by distillation in vacuo. Bp.: 100°-110° C./0.5 Hgmm, $n^{20}_D = 1.5173$.

An etheral solution of the above base is acidified to pH 2 by adding an etheral oxalic acid solution. The precipitated oxalate is filtered and dried. Mp.: 144°-146° C. (ethyl-acetate).

EXAMPLE 3

To a solution of 19.62 g (0.1 mole) of deoxybenzoine in 130 ml methanol 7.8 g (0.13 mole) of n-propyl-amine and after standing for some hours 3.78 g (0.1 mole) of sodium borohydride are added. The reaction mixture is allowed to stand and thereafter evaporated. The residue is taken up in water and extracted with benzene. The benzene solution is acidified with 10% hydrochloic acid under stirring. The precipitated crystalline N-propyl-1,2-diphenyl-ethylamine-hydrochloride is filtered and dried. Mp.: 229°-231° C. (ethanol-ether).

EXAMPLE 4

11.0 g (0.068 mole) of benzyl-propyl-ketone are dissolved in 110 ml of benzene, whereupon 8.0 g (0.135 mole) of n-propyl-amine and 22.6 g (0.2 mole) of anhydrous calcium chloride are added to the solution. The reaction mixture is stirred at 40°-50° C. for 6 hours, then filtered and evaporated. The crude ketimine thus obtained is dissolved in 120 ml of methanol, whereupon 6.4 g (0.17 mole) of sodium borohydride are added. The reaction mixture is allowed to stand, whereupon it is poured into 500 ml of water and extracted five times with 100 ml of benzene each. The benzene solution is dried and evaporated. The crude N-propyl-1-phenyl-2-pentylamine thus obtained is purified by distillation in vacuo. B.p.: 112°-120° C./7 Hgmm, $n^{20}_D = 1.5030$.

The ethyl acetate solution of the above base is acidified by adding ethanol containing hydrochloric acid. The precipitated hydrochloride is purified and dried. Mp.: 122°-124° C. (ethanol-ether).

EXAMPLE 5

To a solution of 21.03 g (0.1 mole( of 1,3-diphenyl-acetone in 140 ml of 96% ethanol 11.8 g (0.2 mole) of n-propylamine are added, the mixture is stirred for an hour, whereupon 3.5 g of amalgamated aluminum foils are added. The reaction mixture is stirred at 55° C. for 20 hours, filtered and evaporated. The residue is dissolved in benzene and acidified under stirring with 10% hydrochloric acid. The precipitated crystalline N-propyl-1,3-diphenyl-2-propylamine-hydrochloride is filtered and dried. Mp.: 174°-176° C. (ethanol-ether).

EXAMPLE 6

To a solution of 29.6 g (0.2 mole) of benzyl-ether-ketone in 200 ml of 96% ethanol 34 ml (0.5 mole) of propyl amine are added, the mixture is stirred for an hour, whereupon 6.75 g of amalgamated aluminium foils are added. The reaction mixture is stirred at 55° C. for 5 hours, whereupon 60 ml of a 40% sodium hydroxide solution are added under stirring. The mixture is filtered and the filtrate is evaporated. The residue is taken up in benzene, washed with water and extracted with 150 ml of 10% hydroxhloric acid. The acidic solution is made alkaline with a 40% sodium hydroxide solution, extracted with benzene, the benzene solution is dried and evaporated. The residual N-propyl-1-phenyl-2-butyl-amine is purified by distillation in vacuo. Bp.: 84°-88° C./0.5 Hgmm, $n^{20}_D = 1.4956$.

The above base is dissolved in ether and the solution is acidified by adding ethanol containing hydrochloric acid. The precipitated crystalline hydrochloride is filtered and dried, mp.: 98°-100° C. (ethyl-acetate).

EXAMPLE 7

To a solution of 67.5 g (0.5 mole) of 1-phenyl-2-propyl-amine in 340 ml of benzene 17.0 g (0.074 mole) of 2-methoxyethyltosylate (J. Org. Chem. 9, 235 1944) are added. The reaction mixture is heated to boiling for 3 hours, and evaporated. The residue is taken up in benzene, extracted with 100 ml of a 10% sodium hydroxide solution and washed with 700 ml of water. The benzene phase is dried and evaporated. The residual crude N-(2-methoxyethyl)-1-phenyl-2-propyl-amine is purified by distillation in vacuo. B.p.: 94°-102° C./8 Hgmm, $n^{20}_D = 1.5012$.

The etheral solution of the above base is acidified with ethanol containing hydrochloric acid. The precipitated crystalline hydrochloride is filtered and dried. M.p.: 115°-118° C. (acetone).

EXAMPLES 8-14

The following compounds enumerated in Table 1 are prepared in an analogous manner to Examples 1-7.

TABLE 1

| Example No. | $R^1$ | $R^2$ | B.p. °C./Hgmm | $n_D^{20}$ | Acid used for salt transformation | M.p. °C. | Recryst. solvent |
|---|---|---|---|---|---|---|---|
| 8 | $C_2H_5$ | $C_2H_5$ | — | — | HCl | 145–147 | ethanol-ether |
| 9 | $C_2H_5$ | $C_6H_{11}$ | 137–140/1 | 1,5160 | HCl | 202–203 | acetone-ethanol |
| 10 | $C_3H_7$ | $CH_3$ | 47–50/15 | 1,4203 | HCl | 125.5 | ethanol-ether |
| 11 | $C_4H_9$ | $C_3H_7$ | — | — | HCl | 78–80 | ethyl-acetate |
| 12 | $C_4H_9$ | $CH(CH_3)CH_2C_6H_5$ | — | — | HCl | 174–176 | ethyl-acetate |
| 13 | $C_6H_{13}$ | $C_3H_7$ | 118–126/0,2 | — | $(COOH)_2$ | 118–120 | i-propanol |
| 14 | $CH_3$ | $(CH_2)_2Br$ | — | — | HBr | 148–150 | acetonitrile |

In the following Examples the preparation of pharmaceutical compositions comprising as active ingredient a compound of the Formula I or IX, respectively, is described. As active ingredient the product of Example 4 is used, but any other compound of the Formula I or IX may be applied as well.

EXAMPLE 15

Hard gelatine capsules having the following composition are prepared:

| Component | Amount. mg/capsule |
|---|---|
| N-propyl-1-phenyl-2-pentyl-amine-hydrochloride | 30.0 |
| Maize starch | 67.0 |
| Avicel | 50.0 |
| Lactose | 50.0 |
| Polyvinyl pyrrolidone | 1.0 |
| Talc | 2.0 |
| Total weight | 200.0 |

The capsules are prepared as follows (for 1000 capsules)

30.0 g of the active ingredient are homogenized with 67.0 g of maize starch, 50 g of Avicel and 50 g of lactose. The homogeneous powder mixture is granulated with an alcoholic polyvinyl pyrrolidone solution on a sieve No. 18, dried and re-granulated on a sieve No. 24. After re-granulation the talc is added and the granules thus obtained are filled into "Snap fit No. 1" capsules either manually or on a machine. The capsules are made free of dust, polished and packed.

EXAMPLE 16

Suppositories having the following composition are prepared:

| Component | Amount, mg/suppository |
|---|---|
| N-propyl-1-phenyl-2-pentylamine-hydrochloride | 25.0 |
| Massa Estarinum ® C (1) | 2975.0 |
| Total weight | 3000.0 |

(1) = Adeps solidus hartfett DAB (Dynamit Nobel)

The suppositories are prepared as follows (for 1000 suppositories):

2975 g of Massa Estarinum ® C are weighed in a duplicator adjusted to 39°–40° C. and melt. To the melt suppository mass 25 g of the active ingredient are added and stirred until it is completely dissolved (about 5–10 minutes). From the melt suppositories weighing 3.0 g are casted. After cooling the excess of the suppository mass is removed. The ready-for-use suppositories are removed from the form and packed.

EXAMPLE 17

Dragées (coated pills) having the following composition are prepared:

| Component | Amount mg/dragée core |
|---|---|
| N-propyl-1-phenyl-2-pentylamine-hydrochloride | 30 |
| Maize starch | 51 |
| Lactose | 82 |
| Luviscol VA64 | 4 |
| Stearin | 4 |
| Avicel | 25 |
| Talc | 4 |
| Total weight: | 200 |

The dragée core is prepared as follows:

The active ingredient, the maize starch and the lactose are homogenized (mixture I). The Luviscol and stearin are dissolved in isopropanol (solution II).

The homogeneous powder mixture (I) is granulated with the isopropanol solution (II). The granules are dried and re-granulated on a sieve No. 16. The Avicel and talc are added and homogenized. Dragée cores are prepared by using a convex die having a diameter of 10 mm. The dragée core thus obtained can be coated with a syrup or film layer by conventional methods (e.g. E. Pandula, G. Takács. Industrial Pharmacy (Ipari Gyó gyszerézet), Medicina, Budapest (1964); H. A. Lieberman, L. Lachmann: Pharmaceutical dosage forms, Marcel Dekkar, Inc. N.Y. (1982))

EXAMPLE 18

Tablets having the following composition are prepared:

| Component | Amount, mg/tablet |
|---|---|
| N-propyl-1-phenyl-2-pentylamine-hydrochloride | 30 |
| Maize starch | 29 |
| Lactose | 24 |
| Maize starch | 9 |
| Gelatine alba | 3 |
| Talc | 3 |
| Magnesium stearate | 2 |
| Total weight: | 100 |

The tablets are prepared as follows:

The active ingredient, maize starch and lactose are sieved and homogenized, whereupon the mixture is granulated with an about 5% aqueous gelatine solution. The granules are dried to a moisture content of 2% and re-granulated on a sieve No. 18. To the granules as external phase the remaining part of maize starch, talc and magnesium stearate are added and from the mixture tablets are pressed by using a die having a diameter of 8 mm.

EXAMPLE 19

Ampoules having the following composition are prepared:

| Component | Amount |
|---|---|
| N-propyl-1-pheny-2-pentylamine-hydrochloride | 30.0 mg |
| Sodium chloride | 8.9 mg |
| Ammonium hydroxide solution 1.7% | q.s |
| Distilled water per injection | ad 1.00 ml |

The ampouls are prepared as follows (for 1000 ampouls).

30.0 g of the active ingredient and 8.9 g of sodium chloride are dissolved in 800 ml of distilled water suitable for injection purposes. The pH of the solution is adjusted to 3.0–8.0 by adding a 1.7% ammonium hydroxide solution. The solution is filled up to 1000.0 ml with distilled water suitable for injection purposes. The microorganism content of the solution is decreased by means of bacterial filtration before filling to ampouls and sterilization.

The filtered solution is immediately filled into suitable ampoules which are then sealed. The ampouls are sterilized. Further manufacture is carried out by conventional methods of the pharmaceutical industry.

II. BIOLOGICAL EXAMPLES

II/1. Determination of noradrenaline releasing effect in cats (in vivo)

The condition of the nicitating membrane of an anesthetized cat is continuously registered by the aid of an auxotonic writing lever kymograph. Releases of noradrenaline induce contractions of the the nictitating membrane in a dose-dependent manner. The i.p. administration PEA induces contractions of the nictitating membrane which is transient in nature. Amphetamine and methamphetamine, however, cause contraction of long duration. In the above test the compounds of the Formula I do not cause any contraction. (Method: J. Knoll: Monoamine Oxidase and Its Inhibition (Eds Wolstenholme and Knight), Elsevier, 1976, page 131).

II/2. Determination of psychostimulant effect in rats a) Modified jumping test (J. Knoll and B. Knoll: Arch. Int. Pharmacody. 148, 200 (1964).

In this test small doses of amphetamine (up to 1–2 mg/kg) improve while larger doses of amphetamine (above 3 mg/kg) deteriorate learning and retention in a dose-dependent manner. The compounds of the Formula I give rise to an improvement of performance at a dose of 0.5–15 mg/kg in a dose-dependent manner. Thus the new compounds are devoid of the performance deteriorating effect characteristic of high doses of amphetamine due to an activation of the serotonergic system (doses above 10 mg/kg are considered to be very high).

b) Shuttle-box text (Method: B. Knoll, J. Knoll: Pol. J. Pharmacol. Pharm. 34, 17–23 1982)

According to this test the daily administration of 1 mg/kg s.c. dose of amphetamine significantly increases the acquizition of a conditioned reaction and its retention during the five days of observation. The increase of performance is however accompanied by a disproportionately high intersignal reaction. The effect of higher amphetamine doses (5–10 mg/kg) can not be even evaluated in the shuttle-box because of an extremely high general motility increasing effect.

The daily administration of 0.5 mg/kg of the compound according to Example 4 gives rise to a significant increase of performance over the control without signs of increased general motility.

Compound according to Example 4 increased learning and retentions from the very first day during the complete test-period, even when administered in an extreme high daily dose of 15 mg/kg. Whereas the performance of these animals is unusually efficient, the increase of the intersignal reactions can be deemed as moderate, when taking into consideration the extremely high performance. Animals treated with a dose of 15 mg/kg of the compound according to Example 4 completely maintain the performance acquired at the end of the one-week learning period even for 6 weeks after the termination of the treatment. According to the tests the compounds of the present invention bring about an extremely high learning performance increasing effect, the said effect being very strong and broad but corresponding to an other mechanism than the activity of amphetamine.

II/3 Determination of antagonism of tetrabenzine-induced depression, in learning test, on rats a) Jumping test Method: J. Knoll, B. Knoll: Arzneimittel Forschung 8, 339 (1958), 9, 633 (1959).

The solid conditioned reflex acquired on the jumping test can not be inhibited even with high doses of the compounds of the Formula I (e.g. with a dose of 15 mg/kg of compound according to Example 6). The reflex can be completely inhibited only with high doses of tetrabenazine (5 mg/kg) while the depressive effect of tetrabenazine can be entirely antagonized by a dose of 15 mg/kg of the compound according to Example 6.

b) Shuttle-box test

Method: B. Knoll, J. Knoll: Pol. J. Pharmacol. Pharm. 34, 17–23 (1982).

According to this test depression caused by tetrabenazine can be antagonized by the compounds of the Formula I. In Table 3 the numerical values of the series of test carried out by using the compound according to Example 6 are disclosed.

Similar results are obtained when using the compounds according to Examples 4 and 14.

TABLE 3

C = control (physiological sodium chloride solution, s.c., daily, N = 12);
T = 0.5 mg/kg of tetrabenazine, s.c., daily N = 12;
V = 0.5 mg/kg of tetrabenazine + 10 mg/kg of compound according to Example 7, s.c., daily, N = 12.

| Learning | | Response to stimulus | | | |
|---|---|---|---|---|---|
| | | F+ | f+ | f− | IR |
| 1st day | C | 29.67 | 51.67 | 18.67 | 9.25 |
| | | ±6.31 | ±6.62 | ±7.96 | ±2.39 |
| | T | 9.58 | 31.25 | 59.17 | 10.25 |
| | | ±3.74 | ±9.20 | ±11.68 | ±2.45 |
| | V | 34.60 | 49.80 | 16.40 | 10.50 |
| | | ±7.00 | ±7.08 | ±10.18 | ±2.05 |
| 2nd day | C | 53.33 | 25.25 | 21.42 | 11.00 |
| | | ±9.87 | ±6.01 | ±10.84 | ±2.51 |
| | T | 8.50 | 30.75 | 60.75 | 8.33 |
| | | ±3.68 | ±9.81 | ±11.81 | ±2.34 |
| | V | 62.20 | 21.00 | 16.80 | 14.70 |

TABLE 3-continued

C = control (physiological sodium chloride solution, s.c., daily, N = 12);
T = 0.5 mg/kg of tetrabenazine, s.c., daily N = 12;
V = 0.5 mg/kg of tetrabenazine + 10 mg/kg of compound according to Example 7, s.c., daily, N = 12.

| Learning | | Response to stimulus | | | |
|---|---|---|---|---|---|
| | | F+ | f+ | f− | IR |
| 3rd day | C | 58.25 ±11.39 | 31.17 ±7.17 | 10.58 ±11.45 | 13.83 ±5.27 |
| | T | 11.42 ±10.43 | 15.83 ±8.35 | 72.75 ±6.46 | 4.67 ±4.00 |
| | V | 69.20 ±4.94 | 9.80 ±6.14 | 21.00 ±11.10 | 21.30 ±1.23 |
| 4th day | C | 66.00 ±11.65 | 28.83 ±3.17 | 5.17 ±12.51 | 13.25 ±7.50 |
| | T | 9.8 ±8.97 | 17.83 ±8.14 | 73.08 ±4.09 | 4.50 ±5.80 |
| | V | 64.90 ±4.02 | 17.70 ±6.81 | 17.40 ±10.63 | 14.30 ±1.31 |
| 5th day | C | 72.25 ±10.92 | 23.33 ±5.21 | 4.52 ±11.66 | 12.83 ±5.06 |
| | T | 17.67 ±7.60 | 12.58 ±6.62 | 69.75 ±3.60 | 6.92 ±4.06 |
| | V | 76.10 ±8.10 | 8.50 ±4.03 | 15.40 ±11.64 | 16.80 ±1.90 |
| | | ±11.29 | ±2.33 | ±10.31 | ±5.78 |

F+ = % of animals showing a conditioned reaction
f+ = % of animals responding to unconditioned stimulus.
f− = % of animals which do not respond even to unconditioned stimulus.
IR = number of intersignal reactions.

II/4. Determination of effect exerted on motility, on rats

The test is carried out in a Shuttle-box without introducing current and light. The number of spontaneous passings over from side of the box to the other is registered and summarized by the apparatus for an observation period of 30 minutes. The test is carried out on groups comprising 112 CFY rats of both sexes weighing 180-200 each. The test compound of the Formula I is added prior to the test subcutaneously, together with tetrabenzine and desmethyl-imipramine (DMI) reference compounds, respectively.

According to this test the compounds of Examples 3 and 6 do not increase motility in a dose of 10 mg/kg, while compounds of Examples 4, 5 and 11 do increase motility in the same dose. The motility inhibiting effect of 1 mg/kg of tetrabenazine is significantly antagonized by a 2.5 mg/kg dose of compound of Example 6 and completely antagonized already by a 1 mg/kg dose of compound of Example 4. In this test, DMI is inhibitory by itself rather than antagonistic against tetrabenzaine induced depression of motility.

II/5. Determination of the effect exerted on metabolism, in rats

Method: B. Issekutz, B. Issekutz, Jr.: Naumyn. Schiedeberg 2 Arch Pharmac 306 (1942).

In this test the compounds of the general Formula I increase metabolism in a significantly lower extent and for a shorter period of time than either amphetamine or l-deprenyl.

II/6. Determination of the effect exerted on food intake, in rats

On well-fed satiated animals a 15 mg/kg p.o. or s.c. dose of the compound according to Example 7 does not change food intake (amphetamine exhibits an anorectic effect already in a dose of 1 mg/kg). In a similar dose it does not influence the food intake of rats fasted for 96 hours, which could be completely inhibited by a 2-5 mg/kg dose of amphetamine for 3-4 hours.

A 5 mg/kg dose of the compounds according to Examples 4 and 13 give rise to a decreasing effect being approximately identical with that of about 0.5 mg/kg of amphetamine, in the first hour.

II/7. Determination of $^3$H-noradrenaine uptake in the nucleus free supernatant of rat cortex (in vivo)

In cortex is homogenized in 0.32M saccharose with a teflon potter, the cell nucleus is sedimented by centrifuging at 0° C. with 1000 g for 20 minutes; the supernatant thus obtained is used for the test. The intake is accomplished in a Krebs-Heinseleit solution saturated with carbogen, in a final volume of 1 ml, at a $^3$H-noradrenaline concentration of $5.10^{18}$ moles. Pre-incubation and incubation are carried out at 37° C. for 5 minutes each. The reaction is stopped by adding 4 ml of ice-cold Krebs solution and the tissue is separated by GF/B filtration. Non-specific uptake is determined by using $10^{-4}$M nisoxetine at 37° C. The radioactivity of the GF/B filter-paper is determined by liquid scintillation measurement in a toluene-PPO-POPOP-tritone mixture.

The results are summarized in Table 4.

Table 4

| Compound | IC$_{50}$ (M) |
|---|---|
| DMI | $10^{-9} - 5 \times 10^{-9}$ |
| Compound according to Example 4 | $5 \times 10^{-8}$ |
| Compound according to Example 6 | $5 \times 10^{-7}$ |
| Compound according to Example 14 | $1 \times 10^{-7}$ |
| l-deprenyl | $7 \times 10^{-6}$ |

Determination of the dopamineric activity increasing effect, on isolated rat striatum preparations Method: Kerecsen et al: Chromatography, the State of the Art, (Eds.Kalász, Ettre) Akadémiai Kiadó Budapest (1985) page 195-203.

In ex vivo tests the animals are treated s.c. for 3 weeks and the organ is removed 2 hours after administering the last injection.

The results are summarized in Tables 5 and 6.

TABLE 5

Change of the dopamine (DA) an DOPAC concentration of the bath of the organ. in vitro (pmole g$^{-1}$ min $^{-1}$)

| Test compound | Dose | DA | DOPAC |
|---|---|---|---|
| Control | — | 91 | 258 |
| Example 6 | 0.3 | 214$^x$ | 172$^x$ |
| | 1.0 | 366$^x$ | 190$^x$ |
| | 3.0 | 290$^x$ | 331$^x$ |
| | 10.0 | 477$^x$ | 537$^x$ |

$^x$statistically significant

TABLE 6

Change of the dopamine (DA) an DOPAC concentration of the bath of the organ, ex vivo (pmole g$^{-1}$ min $^{-1}$

| Test compound | Daily dose | DA | DOPAC |
|---|---|---|---|
| Control | — | 91 | 258 |
| Example 7 | 0.25 | 257$^x$ | 222 |
| | 5.0 | 189$^x$ | 223 |

$^x$statistically significant

II/8. Acute toxicity (on rats)

The results are summarized in Table 7.

TABLE 7

| Test compound Example No. | LD$_{50}$ mg/kg | | |
|---|---|---|---|
| | i.v. | s.c. | p.o. |
| 1 | — | 135 | — |
| 2 | 50 | >200 (%) | — |
| 3 | — | 75 (0%)$^x$ | — |
| 4 | 27 | 50 | 270 |
| 5 | — | >150 (0%) | — |
| 6 | 40 | 140 | 300 |
| 7 | — | >200 (0%) | — |
| 8 | 46 | 195 | — |
| 9 | — | 160 | — |
| 10 | 18 | 175 | — |
| 11 | — | 110 | — |
| 12 | 16 | >25$^x$ | — |
| 13 | — | >50 (0%)$^x$ | — |
| 14 | — | >200 (0%) | — |

$^x$a more concentrated solution cannot be prepared.

II/9 Inhibition of the noradrenaline releasing effect of tyramine, on a rabbit pulmonary artery preparation (in vitro)

Method: J. Knoll: J. Neurl. Transm. 43 177 (1978)

The test comprises the following steps:

1) Taking a control tyramine curve, in cumulative dosage (tyramine doses 1, 3, 8, 18 ug/ml).

2) After washing for 20 minutes, a control tyramine curve is taken again.

3) Equilibration with a single dose of the test compound of the Formula I for 30 minutes.

4) Taking a tyramine curve in the presence of the test compounds, as described in Par. 1).

5) After washing for 20 minutes, a tyramine curve is taken again. The results are summarized in Table 8.

TABLE 8

| Test compound Example No. | IC$_{50}$ (M) | r$^2$ |
|---|---|---|
| 1 | 7.47 × 10$^{-6}$ | 0.78 |
| 2 | 3.68 × 10$^{-7}$ | 0.77 |
| 3 | 7.47 × 10$^{-6}$ | 0.80 |
| 4 | 1.22 × 10$^{-6}$ | 0.77 |
| 6 | 8.46 × 10$^{-7}$ | 0.61 |
| 7 | 1.41 × 10$^{-5}$ | 0.74 |
| 8 | 1.89 × 10$^{-6}$ | 0.7 |
| 9 | 7.99 × 10$^{-7}$ | 0.69 |
| 10 | 1.80 × 10$^{-6}$ | 0.69 |
| 11 | cannot be given | |
| 12 | 3.46 × 10$^{-6}$ | 0.96 |
| 13 | 5.01 × 10$^{-7}$ | 0.80 |
| 14 | cannot be given | |

What we claim is:

1. A compound of the Formula XII

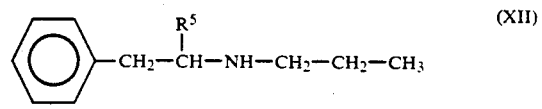

wherein

R$^5$ stands for alkyl having 2-4 carbon atoms.

2. N-propyl-1-phenyl-2-pentylamine or an acid addition salt thereof.

3. N-propyl-1-phenyl-2-butylamine or an acid addition salt thereof.

4. N-propyl-1-phenyl-2-hexylamine or an acid addition salt thereof.

* * * * *